United States Patent
Nebrigic et al.

(10) Patent No.: US 10,940,327 B2
(45) Date of Patent: Mar. 9, 2021

(54) TISSUE TREATMENT APPARATUS AND SYSTEMS WITH PAIN MITIGATION AND METHODS FOR MITIGATING PAIN DURING TISSUE TREATMENTS

(71) Applicant: Solta Medical, Inc., Hayward, CA (US)

(72) Inventors: Dragan D. Nebrigic, Carlsbad, CA (US); Thomas Markiewicz, Los Gatos, CA (US)

(73) Assignee: Solta Medical, Inc., Hayward, CA (US)

( * ) Notice: Subject to any disclaimer, the term of this patent is extended or adjusted under 35 U.S.C. 154(b) by 0 days.

(21) Appl. No.: 16/275,632

(22) Filed: Feb. 14, 2019

(65) Prior Publication Data

US 2019/0175932 A1 Jun. 13, 2019

Related U.S. Application Data

(63) Continuation of application No. 14/339,667, filed on Jul. 24, 2014, now Pat. No. 10,245,440, which is a continuation of application No. 12/649,909, filed on Dec. 30, 2009, now Pat. No. 8,882,758.

(60) Provisional application No. 61/143,537, filed on Jan. 9, 2009, provisional application No. 61/226,138, filed on Jul. 16, 2009.

(51) Int. Cl.
| | |
|---|---|
| *A61N 5/00* | (2006.01) |
| *A61N 1/40* | (2006.01) |
| *A61B 18/14* | (2006.01) |
| *A61B 18/00* | (2006.01) |

(52) U.S. Cl.
CPC .......... *A61N 5/00* (2013.01); *A61B 18/14* (2013.01); *A61N 1/403* (2013.01); *A61B 2018/00011* (2013.01); *A61B 2018/00452* (2013.01); *A61B 2018/1467* (2013.01)

(58) Field of Classification Search
CPC .......... A61B 2018/00452; A61B 2018/00464; A61B 2018/00458; A61B 2018/0047; A61B 2018/142; A61N 5/00; A61N 1/403
See application file for complete search history.

(56) References Cited

U.S. PATENT DOCUMENTS

| | | | | |
|---|---|---|---|---|
| 6,148,232 A | * | 11/2000 | Avrahami | A61N 1/30 600/372 |
| 6,611,706 B2 | * | 8/2003 | Avrahami | A61M 37/0015 600/372 |
| 6,932,812 B2 | * | 8/2005 | Crowley | A61B 18/1492 600/374 |
| 7,422,586 B2 | * | 9/2008 | Morris | A61B 18/1477 606/41 |

* cited by examiner

*Primary Examiner* — Ronald Hupczey, Jr.
(74) *Attorney, Agent, or Firm* — Thompson Hine LLP

(57) ABSTRACT

Methods, apparatus, and systems for delivering electromagnetic energy to a patient's tissue with a reduction in the pain experienced by the patient. Electromagnetic energy is delivered from a treatment electrode through the skin surface to the tissue at a plurality of power levels over a treatment time. During the energy delivery, a portion of the treatment electrode is in a contacting relationship with the skin surface. A tip frame may be disposed between the treatment electrode and the skin surface when the electromagnetic energy is delivered.

12 Claims, 5 Drawing Sheets

TISSUE TREATMENT APPARATUS AND SYSTEMS WITH PAIN MITIGATION AND METHODS FOR MITIGATING PAIN DURING TISSUE TREATMENTS

CROSS-REFERENCE TO RELATED APPLICATIONS

This Application is a continuation of application Ser. No. 14/339,667, filed Jul. 24, 2014, which is a continuation of application Ser. No. 12/649,909, filed Dec. 30, 2009, which issued as U.S. Pat. No. 8,882,758 on Nov. 11, 2014, which claims the benefit of Application No. 61/143,537, filed Jan. 9, 2009 and claims the benefit of Application No. 61/226,138, filed Jul. 16, 2009. Each of these patent documents is hereby incorporated by reference herein in its entirety.

BACKGROUND

The invention generally relates to apparatus, systems, and methods for treating tissue with electromagnetic energy and, more particularly, relates to treatment apparatus, systems, and methods for mitigating patient pain while treating tissue with high frequency electromagnetic energy.

Various cosmetic tissue treatments use energy delivery devices to non-invasively and non-ablatively treat tissue in order to improve a patient's appearance, such as smoothing and tightening skin; contouring along the jaw line and under the chin, and improving skin texture; softening wrinkles around the mouth, eyes and forehead; reducing cellulite; or removing skin spots or hair. These non-invasive, transcutaneous procedures involve no surgery or injections but instead project electromagnetic energy into the tissue. Such non-invasive energy delivery devices may emit the electromagnetic energy in different regions of the electromagnetic spectrum to accomplish the tissue treatment with reduced patient recovery time in comparison with ablative procedures.

Skin is a type of body tissue that includes plural distinct layers. The epidermis constitutes the visible outer layer on the surface. The dermis, which underlies the epidermis, contains collagen fibers, blood vessels, hair follicles, and other skin components. The hypodermis or subcutaneous fat layer, which underlies the dermis, consists of fat tissue and a web of collagen fibers in the form of fibrous septae running through the fat. The fibrous septae secure the dermis to the underlying bone and muscle. Collagen fibers are recognized to be a very flexible and stretchable protein and are characterized by a high tensile strength.

The occurrence of wrinkles is an unavoidable natural process. Wrinkles are primarily associated with advancing age and skin damage arising from exposure to damaging environmental factors. Environmental factors include sun damage from exposure to sunlight, air pollution, smoking, repetitive facial movements such as frowning, and the natural effects of gravity, which cause sagging of the skin with advancing aging. Deteriorating collagen exhibits a loss of elasticity, which results in the formation of rhytids or wrinkling of the epidermis.

Electromagnetic radiation, specifically light and heat, applied to the different layers of the skin can have a physiological effect on the skin's appearance. In particular, electromagnetic energy can arrest the formation of wrinkles and impart a more youthful skin appearance. High frequency treatment devices, such as radio-frequency (RF)-based treatment devices, may be used to treat skin tissue non-ablatively and non-invasively with heat. Such high frequency devices operate by transmitting high frequency energy through the epidermis to the underlying tissue, while actively cooling the epidermis to prevent thermal damage to a depth of the skin tissue near the skin surface. The high frequency energy heats the tissue at depths beneath the cooled region to a therapeutic temperature sufficient to denature the collagen, which causes the collagen fibers in the dermis to shrink and contract. In addition to the tightening of the treated tissue as the collagen fibers contract, treatment with high frequency energy also causes a mild inflammation. The inflammatory response of the treated tissue may cause new collagen to be generated over time, which can result in additional tissue contraction. When the inflammatory response of the treated tissue is highly significant, the new collagen formed is known as scar collagen.

Conventional high frequency treatment devices employ a handpiece, a disposable treatment tip coupled with a nose of the handpiece, and a high frequency generator connected by conductors inside the handpiece with an electrode in the treatment tip. Conventional electrodes consist of a pattern of one or more metallic features carried on a flexible electrically insulating substrate, such as a thin film of polyimide. The substrate contacts the patient's skin surface during treatment and the metallic features reside on the non-contact side of the substrate. The temperature of the treatment tip, which is measured by temperature sensors carried on the treatment tip, is correlated with the temperature of the patient's skin. During the procedure, the doctor controls the energy density of the high frequency power delivered from the electrode with a treatment setting. Treatment tips are frequently intended for single patient use and, therefore, are not reusable. Following the patient treatment, the doctor or treatment technician removes the treatment tip from the handpiece and, if disposable, discards it.

Patient pain is inherent in tissue treatments using electromagnetic energy. Patient pain is typically regulated to optimize the treatment result while also minimizing patient discomfort to make the procedure tolerable. A patient may be given an oral pain medication and/or a local topical anesthesia cream may be applied as a numbing agent. At the inception of the treatment procedure, the doctor will initially administer the high frequency energy at a treatment setting to one or more test sites and monitor patient feedback on the heat sensation associated with the treatment setting being used. A tolerable, yet comfortable, treatment setting for the treatment procedure is established based upon the patient feedback from the test sites.

The treatment electrode used in the treatment includes a conductor region delimited by an outer peripheral edge. For monopolar energy delivery, an edge effect has been observed at the outer peripheral edge that causes the energy density of the high frequency energy delivered to the tissue to be non-uniform across the surface area of the treatment electrode. Specifically, the energy density is highest near the peripheral edge of the electrode. As a result, tissue proximate to the outer peripheral edge of the electrode is heated to a higher temperature than tissue proximate to the interior surface area of the electrode. The higher temperatures near the peripheral edge form hot spot thermal zones that are a highly likely source of heat-related pain perceived by the patient. Because patient discomfort is linked with the treatment setting, reducing the treatment level to counteract the edge effect effectively reduces the average energy density for the high frequency energy delivered during the treatment procedure.

In general, treatment results and the chance for pain or discomfort will scale with the treatment setting used by the doctor. What is needed, therefore, are apparatus and methods for reducing the pain associated with such tissue treatments so that patient discomfort is alleviated and therapeutic results can be improved by increasing the treatment setting and the amount of heat delivered to the skin.

SUMMARY

Embodiments of the invention are generally directed to methods, apparatus, and systems for transcutaneously delivering electromagnetic energy to treat patient tissue underlying a skin surface, particularly during non-invasive and non-ablative therapeutic tissue treatments, with reduced patient pain.

In one embodiment, a method is provided for operating a tissue treatment apparatus to transcutaneously treat tissue located beneath a skin surface with electromagnetic energy delivered from a treatment electrode. The method includes contacting a portion of the treatment electrode with the skin surface and, while maintaining the contact between the portion of the treatment electrode and the skin surface, delivering the electromagnetic energy from the treatment electrode through the skin surface to the tissue at a plurality of differing power levels over a treatment time. Preferably, a magnitude of the power at each of the power levels incrementally decreases with increasing (i.e., accumulating) treatment time. The progressive change in the power level operates to reduce patient pain so that a greater amount of heat delivered to the skin.

In another embodiment, a system is provided for transcutaneously treating tissue located beneath a skin surface with electromagnetic energy. The system includes a handpiece and a treatment tip coupled in a removable manner with the handpiece. The treatment tip includes a treatment electrode having a portion configured to be placed in a contacting relationship with the skin surface. The treatment electrode is configured to deliver the electromagnetic energy through the skin surface to the tissue. The system further includes a generator electrically coupled with the treatment electrode and a controller in operative connection with the generator. The generator is adapted to energize the treatment electrode to deliver the electromagnetic energy from the treatment electrode to the tissue. The controller is configured to deliver the electromagnetic energy from the treatment electrode through the skin surface to the tissue at a series of power levels over a treatment time while the portion of the treatment electrode is in contact with the skin surface.

In another embodiment, an apparatus is provided for a treatment tip used in treating tissue located beneath a skin surface. The treatment tip has a treatment electrode configured to deliver electromagnetic energy transcutaneously through the skin surface to the tissue. The apparatus includes a sleeve, which is composed of an electrically-insulating material, coupled with the treatment tip. The sleeve includes a frame and an aperture in the frame that exposes a portion of the treatment electrode. The frame is disposed between the treatment electrode and the skin surface when the electromagnetic energy is transcutaneously delivered from the treatment electrode through the skin surface to the tissue.

In yet another embodiment, a method is provided for operating a tissue treatment apparatus to transcutaneously treat tissue located beneath a skin surface with electromagnetic energy delivered from a treatment electrode. The method includes contacting a portion of the treatment electrode with the skin surface and separating a different portion of the treatment electrode from the skin surface with a spacer. While maintaining the contact between the portion of the treatment electrode and the skin surface, the electromagnetic energy is transcutaneously delivered from the treatment electrode through the skin surface to the tissue.

DETAILED DESCRIPTION

Figure 1:
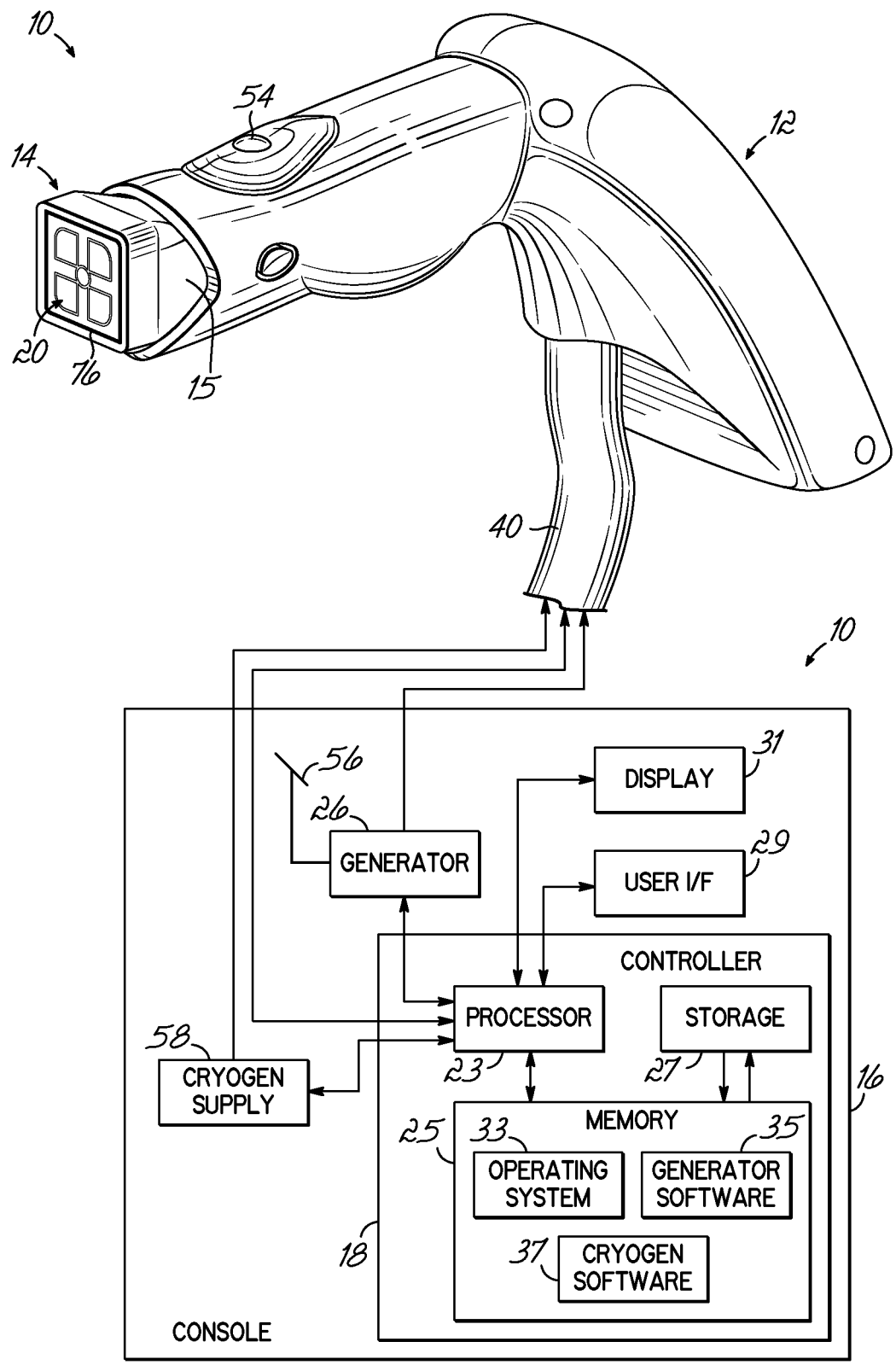
FIG. 1 is a diagrammatic view of a treatment system with a handpiece, a treatment tip, and a console in accordance with an embodiment of the invention.
Figure 2:
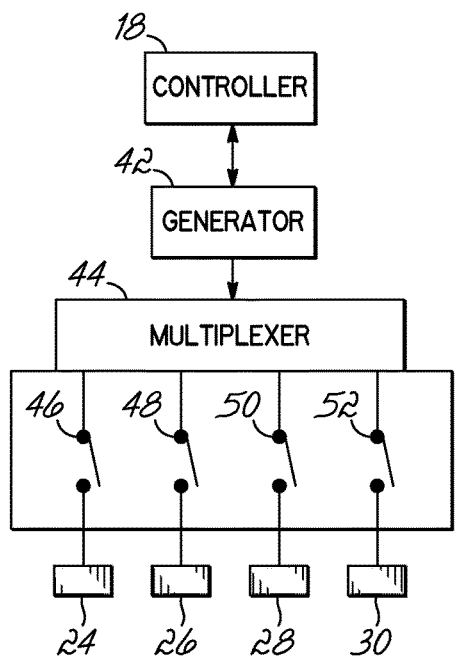
FIG. 2 is a diagrammatic view of a portion of the treatment system of FIG. 1.
Figure 3:
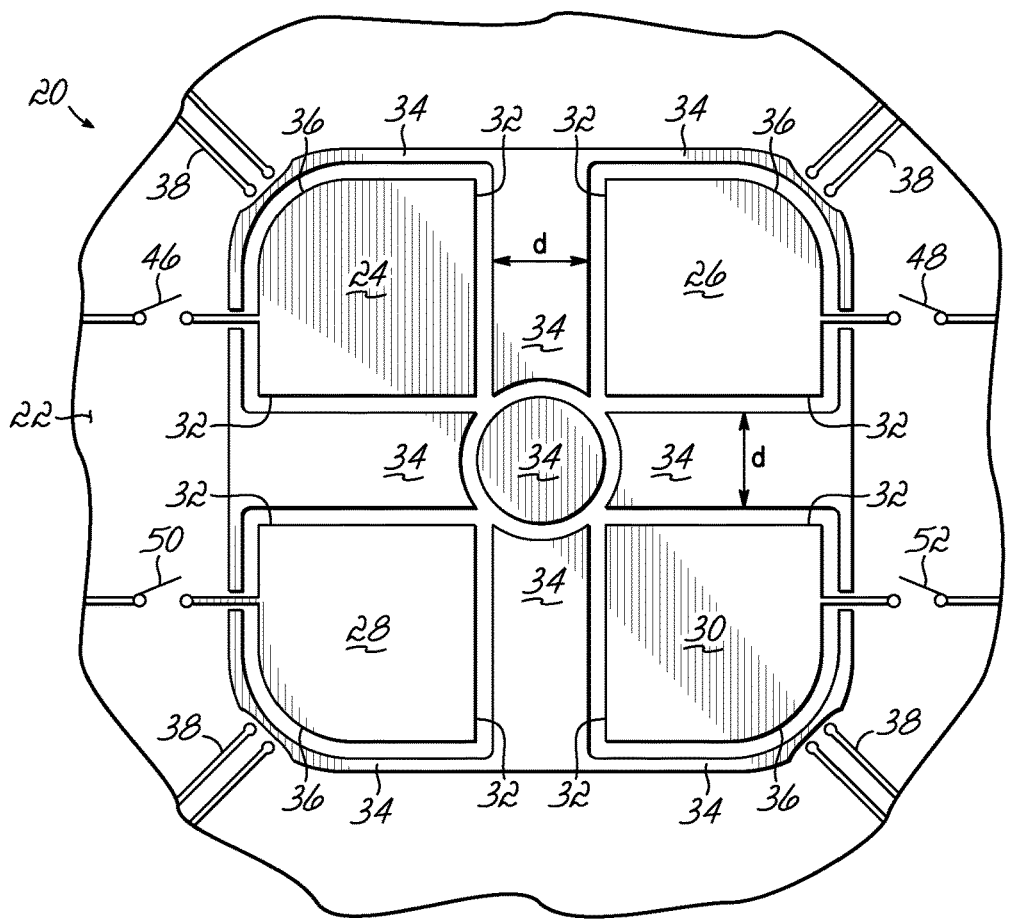
FIG. 3 is a rear view of the treatment electrode of FIG. 1.

With reference to FIGS. 1-3, a treatment apparatus 10 generally includes a handpiece 12, a treatment tip 14 coupled in a removable and releasable manner with the handpiece 12, a console generally indicated by reference numeral 16, and a system controller 18. The system controller 18, which is incorporated into the console 16, orchestrates the global operation of the different individual components of the treatment apparatus 10. Under the control of the system controller 18 and any operator interaction with the system controller 18 at the console 16 and with controls at the handpiece 12, the treatment apparatus 10 is adapted to non-invasively and non-ablatively deliver electromagnetic energy in a high frequency band of the electromagnetic spectrum, such as the radiofrequency (RF) band, to a region of a patient's tissue. The delivered energy heats the tissue to a targeted temperature range. The elevation in temperature may produce for example, changes in collagen fibers that achieve a desired treatment result, such as removing or reducing wrinkles and otherwise tightening the skin to thereby improve the appearance of a patient receiving the treatment. In alternative embodiments, the treatment apparatus 10 may be configured to deliver energy in the infrared band, microwave band, or another high frequency band of the electromagnetic spectrum, rather than within the RF band, to the patient's tissue.

The treatment tip 14 includes a housing 15 and a treatment electrode 20 supported by the housing 15. The treatment electrode 20, which has a portion that directly contacts the skin surface, may assume the representative form of an electrically-insulating substrate 22 and a plurality of active electrodes 24, 26, 28, 30 carried on the electrically-insulating substrate 22. Each of the active electrodes 24, 26, 28, 30 can be individually powered to deliver electromagnetic energy to the tissue. The substrate 22 is composed of a non-conductive dielectric material and the active electrodes 24, 26, 28, 30 are composed of an electrical conductor. The active electrodes 24, 26, 28, 30 are positioned on the substrate 22 such that one of the active electrodes 24, 26, 28, 30 is disposed in each of the four quadrants of the treatment electrode 20. The active electrodes 24, 26, 28, 30, which are electrically isolated from each other and are composed of an electrical conductor, may have identical surface areas or different surface areas. In one embodiment, each of the individual active electrodes 24, 26, 28, 30 has a surface area of about three $mm^2$. Inside edges 32 of the active electrodes 24, 26, 28, 30 are separated from each another by a small but significant distance, d. Electrically isolated and thermally conductive metal sections 34 are provided near the outside edges 36 of the active electrodes 24, 26, 28, 30.

The treatment tip 14 includes temperature sensors 38, such as thermistors or thermocouples, that are constructed to sense the temperature at each of the four corners of the treatment electrode 20. The measured temperature reflects the temperature of the treated tissue and may be used as feedback in a control loop controlling energy delivery and/or cooling of the skin surface. The handpiece 12 or treatment tip 14 may also include pressure sensors (not shown) for detecting physical contact between the treatment electrode 20 and the skin surface of the patient.

The active electrodes 24, 26, 28, 30 are physically carried on a side of the substrate 22 that does not contact the skin surface and is therefore separated by the substrate 22 from the skin surface. In one embodiment, the substrate 22 of the treatment electrode 20 may comprise a thin flexible base polymer film carrying the active electrodes 24, 26, 28, 30 and thin conductive (e.g., copper) traces or leads on the substrate 22 that electrically couple the active electrodes 24, 26, 28, 30 with contact pads inside the treatment tip 14. The base polymer film of substrate 22 may be, for example, polyimide or another material with a relatively high electrical resistivity and a relatively high thermal conductivity. The conductive leads may contain copper or another material characterized by a relatively high electrical conductivity.

The treatment tip 14 may include a different number of active electrodes than the total of four active electrodes 24, 26, 28, 30. The active electrodes 24, 26, 28, 30 can be sized such that a maximum power to energize any single electrode is approximately equal to the maximum power output of the high frequency generator 42. In this example, the maximum power to energize any two of the active electrodes 24, 26, 28, 30 would exceed the maximum power output of the high frequency generator 42. According to an alternative embodiment, the active electrodes 24, 26, 28, 30 may be made smaller in size, and groups of the active electrodes 24, 26, 28, 30 may be sequentially powered, with the power required to energize any single group being slightly less than the maximum output power of the generator 42.

In various embodiments, each of the active electrodes 24, 26, 28, 30 may have a surface area greater than about 1 $cm^2$ and, in particular, each of the active electrodes 24, 26, 28, 30 may have a surface area in the range of about 1 $cm^2$ to about 20 $cm^2$. In specific embodiments, each of the active electrodes 24, 26, 28, 30 may have a surface area of about 1 $cm^2$, about 1.5 $cm^2$, about 3 $cm^2$, about 5 $cm^2$, about 7 $cm^2$, about 10 $cm^2$, about 15 $cm^2$, or about 20 $cm^2$.

The active electrodes 24, 26, 28, 30 are electrically coupled by a set of insulated and shielded conductors 40 that extend exteriorly of the handpiece 12 to a generator 42 at the console 16. A multiplexer 44 is used to select which of the active electrodes 24, 26, 28, 30 is electrically coupled with the generator 42 at any instant in time. The generator 42 is configured to generate the electromagnetic energy used in the treatment to impart a therapeutic effect to heat target tissue beneath the patient's skin surface. The generator 42, which has the form of a high frequency power supply, is equipped with an electrical circuit operative to generate high frequency electrical current, typically in the radio-frequency (RF) band of the electromagnetic spectrum. The operating frequency of generator 42 may be in the range of several hundred kHz to about twenty (20) MHz. In one embodiment, the generator 42 is a 400 watt, 6.78 MHz high frequency generator. The electrical circuit in the generator 42 converts a line alternating current voltage into drive signals for the treatment electrode 20. The drive signals have an energy content and a duty cycle appropriate for the amount of power and the mode of operation that have been selected by the clinician, as understood by a person having ordinary skill in the art.

The system controller 18 may represent practically any computer, computer system, or programmable device recognized by a person having ordinary skill in the art and capable of carrying out the functions described herein, as will be understood by those of ordinary skill in the art. System controller 18 typically includes at least one processor 23 coupled to a memory 25. Processor 23 may represent one or more processors (e.g., microprocessors), and memory 25 may represent the random access memory (RAM) devices comprising the main storage of system controller 18, as well as any supplemental levels of memory, e.g., cache memories, non-volatile or backup memories (e.g. programmable or flash memories), read-only memories, etc. In addition, memory 25 may be considered to include memory storage physically located elsewhere in system controller 18, e.g., any cache memory in a processor 23, as well as any storage capacity used as a virtual memory, e.g., as stored on a mass storage device 27 or another computer (not shown) coupled to system controller 18 via a network.

System controller 18 also typically receives a number of inputs and outputs for communicating information externally. For interface with a user or operator, system controller 18 typically includes one or more user input devices (e.g., a keyboard, a mouse, a trackball, a joystick, a touchpad, a keypad, a stylus, and/or a microphone, among others) in the form of a user interface 29. System controller 18 may also include a display 31 (e.g., a CRT monitor or an LCD display panel, among others).

System controller 18 operates under the control of an operating system 33, and executes or otherwise relies upon various computer software applications, components, programs, objects, modules, data structures, etc. In general, the routines executed by the system controller 18 to operate the treatment system 10, whether implemented as part of an operating system or a specific application, component, program, object, module or sequence of instructions will be referred to herein as "computer program code". The computer program code typically comprises one or more instructions that are resident at various times in various memory and storage devices in a computer, and that, when read and executed by one or more processors in a computer, causes that computer to perform the steps necessary to execute steps or elements embodying the various aspects of the invention.

The system controller 18 includes digital and/or analog circuitry that interfaces the processor 23 with the generator 42 for regulating the power delivered from the generator 42 to the treatment electrode 20 and with the multiplexer 44 for determining which of the active electrodes 24, 26, 28, 30 is coupled with the generator. Generator software 35 resides as an application in the memory 25 and is executed by the processor 23 in order to issue commands that control the operation of the generator 42. The system controller 18 includes digital and/or analog circuitry that interfaces the processor 23 with a cryogen supply 58, such as a pre-filled canister containing pressurized cryogen, and a control valve for regulating the cryogen delivered to the treatment electrode 20. Cryogen software 37 resides as an application in the memory 25 and is executed by the processor 23 in order to issue commands that control the operation of the cryogen supply 58 and a control valve.

The user interface 29 may be used to deliver instructions to the system controller 18 to adjust the generator 42 and multiplexer 44 and to establish an arbitrary treatment setting based upon operator input at the handpiece 12. The memory 25 may be used to store the parameters of the power profile shown in FIG. 4. System controller 18 may also communicate, for example, with a nonvolatile memory (not shown) carried by the handpiece 12 or with a nonvolatile memory (not shown) carried by the treatment tip 14.

The multiplexer 44 includes switches 46, 48, 50, 52, such as relays or another type of switching device or circuit, that are adapted to be switched between closed and open conditions by the system controller 18. In the closed condition, a signal or current path is established that electrically connects one of the terminals of the high frequency generator 42 and a respective one of the active electrodes 24, 26, 28, 30. In the open condition, the respective one of the active electrodes 24, 26, 28, 30 is disconnected from the high frequency generator 42. The multiplexer 44 may be integrated into the system controller 18, integrated into the generator 42, integrated into the treatment tip 14, or may constitute a separate circuit element controlled by either the system controller 18 or generator 42. The multiplexer 44 permits the active electrodes 24, 26, 28, 30 to be individually energized by the system controller 18 in the closed circuit with the generator 42.

During a non-ablative and non-invasive tissue treatment, a portion of the treatment electrode 20 has a direct contacting relationship with the skin surface of the patient. In the representative arrangement, the substrate 22 is arranged between the active electrodes 24, 26, 28, 30 and the skin surface so that a portion of the substrate 22 directly contacts the skin surface. Electromagnetic energy is transmitted in a transcutaneous manner from each of the active electrodes 24, 26, 28, 30 through the thickness of the portion of substrate 22 to the tissue by capacitive coupling with the tissue of the patient.

An activation button 54, which is accessible to the operator from the exterior of the handpiece 12, is configured to be actuated to close a switch in a normally open circuit with the generator 42. The closed circuit energizes the treatment electrode 20. Actuation of the activation button 54 triggers delivery of the high frequency energy over a short timed delivery cycle from the treatment electrode 20 to the target tissue. After a fixed amount of time has elapsed, the delivery of high frequency energy from the treatment electrode 20 to the tissue at the treatment site is discontinued. The handpiece 12 is manipulated to position the treatment tip 14 near a different treatment site on the skin surface and another cycle of high frequency energy is delivered to the patient's tissue. This process is repeated for an arbitrary number of treatment sites.

High frequency electrical current flowing between the treatment electrode 20 and the patient is concentrated at the skin surface and the underlying tissue across the contacting surface area of the treatment electrode 20. Capacitive coupling of the high frequency electromagnetic energy relies on energy transfer from each of the active electrodes 24, 26, 28, 30 through the dielectric material of the substrate 22 to create an electric field across the surface area where the treatment electrode 20 contacts the patient's body. The time-varying electric field induces electrical currents within the surrounding tissue beneath the skin surface.

Because of the natural resistance of tissue to electrical current flow, volumetric heating results within the tissue. The volumetric heating delivers a therapeutic effect to the tissue at the treatment site. For example, heating to a temperature effective to contract collagen containing tissue at the treatment site, which will result in tissue tightening or another aesthetic effect that improves the patient's appearance. The heating depth in the tissue is based upon the size and geometry of the treatment electrode 20 and, contingent upon the selection and configuration of the treatment tip 14, can be controlled to extend from a few hundred microns beneath the skin surface to several millimeters.

A non-therapeutic passive return electrode 56 is used to electrically couple the patient with the generator 42. During patient treatment, the high frequency current flows from the treatment electrode 20 through the treated tissue and the intervening bulk of the patient to the return electrode 56 and then to the generator 42 through conductors 40 inside a return cable to define a closed circuit or current path. The return electrode 56 is physically attached by, for example, an adhesive bond to a site on the body surface of the patient, such as the patient's back.

The surface area of the return electrode 56 in contact with the patient is relatively large in comparison with the surface area of the treatment electrode 20. Consequently, at the tissue adjacent to the return electrode 56, the current density flowing from the patient to the return electrode 56 is relatively low in comparison with the current density flowing from the treatment electrode 20 to the patient at the treatment site remote from the return electrode 56. Because negligible heating is produced at its attachment site to the patient, a non-therapeutic effect is created in the tissue adjacent to the return electrode 56.

Although the treatment electrode 20 and the return electrode 56 are representatively configured for the delivery of monopolar high frequency energy, the treatment electrode 20 may be configured to deliver bipolar high frequency energy. The modifications to the treatment apparatus 10 required to deliver bipolar high frequency energy are familiar to a person having ordinary skill in the art. For example, the return electrode 56 may be eliminated from the treatment apparatus 10 and a bipolar type of treatment electrode substituted for the monopolar treatment electrode 20.

A control valve (not shown) in either the treatment tip 14 or handpiece 12 is used to deliver a cryogen spray to the back side of the treatment electrode 20 for controlling the temperature of the treatment electrode 20. One purpose of the cryogen spray is to pre-cool the patient's epidermis, before powering the treatment electrode 20, by heat transfer between the treatment electrode 20 and the skin surface. The cooling creates a reverse thermal gradient in the tissue such that the temperature of the tissue at and near the skin surface is cooler than the temperature of the tissue deeper within the epidermis or dermis. As a result, the high frequency energy delivered to the tissue fails to heat all or a portion of the patient's epidermis to a temperature sufficient to cause significant epidermal thermal damage. Depths of tissue that are not significantly cooled by pre-cooling will warm up to therapeutic temperatures, which cause a desired therapeutic effect. The amount and/or duration of pre-cooling may be used to select the protected depth of untreated tissue. The cryogen delivered by the control valve in the treatment tip 14 may also be used to cool portions of the tissue during and/or after heating by the high frequency energy transferred from the treatment electrode 20. Post-cooling may prevent or reduce heat delivered deeper into the tissue from conducting upward and heating shallower tissue regions, such as the epidermis, to temperatures which could thermally damage shallower tissue regions even though external energy delivery to the targeted tissue has ceased.

Various duty cycles of cooling and heating that rely on cooling and high frequency energy transfer from the treatment electrode 20 are utilized contingent upon the type of treatment and the desired type of therapeutic effect. The cooling and heating duty cycles may be controlled and coordinated by operation of the system controller 18. Suitable cryogens include low boiling point fluids, but are not limited to, R134a (1,1,1,2-Tetrafluoroethane) refrigerant, liquid nitrogen, and R152a refrigerant (1,1-Difluoroethane). Heat can be extracted from the treatment electrode 20 by virtue of evaporative cooling of the low boiling point fluid, which cools the treatment electrode 20. In alternative embodiments, the patient's skin and/or the treatment electrode 20 may be cooled in a different manner, such as with a thermoelectric or Peltier device, a closed-loop fluid cooling, or a Zimmer cooler that is configured to deliver a forced stream of cold air onto the skin surface.

Figure 4:
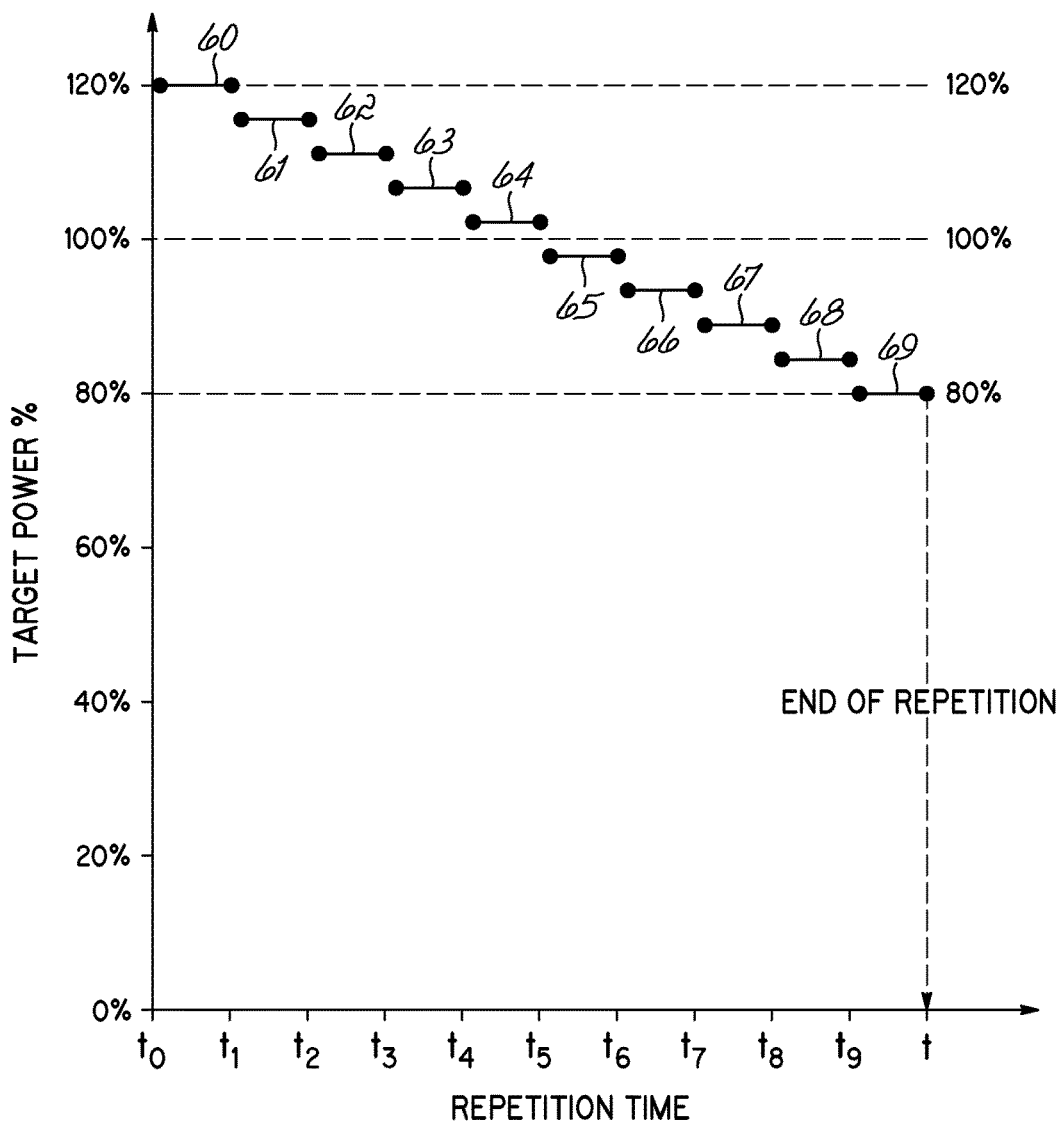
FIG. 4 is a graphical view showing a power profile for use in operating the treatment system of FIGS. 1-3.

With reference to FIG. 4, the power supplied from the generator 42 to each of the active electrodes 24, 26, 28, 30 may be modulated by the system controller 18 to have a characteristic profile of energy delivery as a function of treatment time. Specifically, the profile may contain a plurality of different power levels 60-69 and the system controller 18 may cause the generator 42, which has circuitry known to a person having ordinary skill in the art for adjusting the output power, to sequentially step from one power level to the next power level as time evolves during a treatment repetition with each of the active electrodes 24, 26, 28, 30. A treatment repetition is constituted by the sequential application of power using the power profile of FIG. 4 to one of the active electrodes 24, 26, 28, 30 while maintaining the contacting relationship with the skin surface 82 and the rest of the active electrodes 24, 26, 28, 30 in a non-energized status. In turn, each of the active electrodes 24, 26, 28, 30 is energized using the profile.

The total time, t, for each treatment repetition using any one of the active electrodes 24, 26, 28, 30 is divided into a number, n, of discrete power levels 60-69. In the representative embodiment of FIG. 4, the total treatment time, t, for a single treatment repetition is divided into ten (10) intervals and each of the intervals is characterized by one of the power levels 60-69 associated with it. However, a different number of time intervals and power levels 60-69 may be selected in accordance with the treatment protocol. The duration of each time interval is established as a fraction given by the total time, t, divided by the number, n, of power levels 60-69. In the representative embodiment of FIG. 4, the ten (10) time intervals are of equal duration, although the embodiments of the invention are not so limited to being isochronal. For example, the length of the time intervals may increase with increasing time or, alternatively, may decrease with increasing time.

In the representative embodiment, the applied power differs at each of the power levels 60-69. Generally, a different power need only be applied for at least two of the power levels 60-69. In yet another embodiment, the same power may be applied at two or more, but not all, of the power levels 60-69. For example, the power applied at the initial and second power levels 60 may be the same, and the power applied at each successive power level 60-69 thereafter may decrease in a progressive manner. As another example, the same power may be applied during three power levels, for example power levels 62-64, between the initial power level 60 and final power level 69, and the power applied at the power levels 60, 61 before and the power levels 65-69 after these three power levels 62-64 may progressively decrease.

Over the duration of each of the power levels 60-69, the power at that particular power level 60-69 is maintained constant at a percentage of the target power in the representative embodiment. The transition between each adjacent pair of power levels 60-69 is abrupt and discontinuous as the generator 42 is instructed by the system controller 18 to reduce the power. The power levels 60-69 are applied during a single treatment repetition and without moving the treatment electrode 20 so that electromagnetic energy is sequentially delivered from each of the active electrodes 24, 26, 28, 30 with the treatment electrode 20 stationary and without any quiescent time periods to a region of tissue at each of the power levels 60-69. As a result, each tissue region that is treated received the electromagnetic energy at a series of power levels 60-69 that progressively decrease with increasing treatment time.

The total time, t, for a single treatment repetition of all power levels 60-69 according to FIG. 4 for any one of the active electrodes 24, 26, 28, 30 may range from one (1) to three (3) seconds. As an example, if the total time, t, is one second, the number of time intervals is ten, and the time intervals are of equal duration, then the duration of each time interval is 100 milliseconds. After the lapse of the total time, t, and completion of all of the power levels 60, the power is reduced to zero (0) in anticipation of energizing the next active electrode of the treatment electrode 20 to perform the next treatment repetition or, alternatively, in anticipation of lifting the treatment tip 14 to move to the next treatment location for another series of treatment repetitions.

The power supplied from the generator 42 to any one of the active electrodes 24, 26, 28, 30 during a treatment repetition is bounded in a range bounded by upper and lower limits. The upper and lower limits for this range are denoted, respectively, by a maximum setting for the applied power over the time, t, for a single repetition and a minimum setting for the applied power over the time, t, for a single repetition. In the representative embodiment of FIG. 4, the maximum setting targeted for the power is at least 120% (at least 20% above a nominal power setting) at the initial power level 60 and the minimum setting targeted for the power is at least 80% (at least 20% below the same nominal power setting) at the final power level 69. A typical nominal power setting may be on the order of 200 joules per second and, in alternative embodiments, may be selected as any value less than 400 joules per second effective to achieve a therapeutic effect.

In the representative embodiment depicted in FIG. 4, the maximum power is supplied as the initial power level 60 during the initial time interval and the minimum power is supplied as the final power level 69 during the final time interval. This cascading approach results in the power of the electromagnetic energy delivered at each of the differing power levels 60-69 to decrease with increasing treatment time, t. In one embodiment, the power at each successive power level 60-69 with advancing time is less than the power at the immediately previous power level 60-69 so that the treatment protocol for each of the active electrodes 24, 26, 28, 30 has a descending profile over the total time, t. However, the minimum and maximum powers may be supplied at different time intervals between the initial and final time intervals. For example, the maximum power may be applied as the power level 65 during the sixth time interval. As another example, the minimum power may be applied at the power level 69 for the final time interval and also at the power level 68 for the next to last time interval.

The system controller 18 implements the various parameters of the power profile in FIG. 4 using control signals sent to the generator 42 when power is applied to each of the active electrodes 24, 26, 28, 30 according to the switching by the multiplexer 44. The memory 25 of the system controller 18 stores the various parameters for the power profile. The application of the stepped power profile of FIG. 4 promotes the ability to deliver electromagnetic energy across a larger surface area on the skin surface by decreasing the pain sensitivity of the patient. The power profile of FIG. 4 permits an increase in the total power delivered by each of the active electrodes 24, 26, 28, 30 to the patient's tissue. The power profile is implemented in an open loop control system because there is no feedback provided for control. Instead, the power profile is implemented on a timed basis at the system controller 18.

The use of the power profile of FIG. 4 may be applied to treatment electrodes of relatively large area and/or treatment electrodes that have only a single active electrode, instead of the segmented treatment electrode 20 that has multiple active electrodes 24, 26, 28, 30. For example, the power profile of FIG. 4 may be applied in conjunction with the treatment electrode 20a (FIG. 5) that has a single region composed of electrical conductor defining one active electrode so that each repetition normally includes only a single contact with the skin surface, energy delivery, and lift to move for the next treatment repetition.

In use to perform a treatment procedure and with reference to FIGS. 1-4, the physician selects a type of treatment tip 14 based on the procedure to be performed and the size of the surface area on the patient to be treated, as well as the depth of cooling and heating desired for the treatment procedure. The procedure protocol may include a combination of pulse count, pulse duration, as well as the power levels and heating profile of FIG. 4. After choosing the treatment tip 14 and attaching it to the handpiece 12, the physician marks the intended treatment area on the patient with a grid of removable markings that are easily wiped away post-procedure. Each discrete square in the grid corresponds approximately to the size of the portion of the treatment electrode 20 that is placed in direct contact with the skin surface. The markings operate as a placement guide on the patient's skin surface for the treatment procedure. The return electrode 56 is attached to the patient to supply the current path for the high frequency current back to the generator 42.

After the optional application of a conductive fluid, each square within the grid is sequentially treated with high frequency energy delivered from the treatment electrode 20. Specifically, at each grid square, the physician lands the portion of treatment electrode 20 directly against the patient's skin and actuates the activation button 54 on the handpiece 12, which causes the system controller 18 to direct a metered spray of a cryogen to the backside of the active electrodes 24, 26, 28, 30 for pre-cooling the patient's tissue adjacent to the treatment electrode 20 by heat transfer through the treatment electrode 20. A control valve regulates the delivery of cryogen, which cools and protects the skin's superficial layers proximate to the skin surface. Cooling the epidermis limits the temperature to lessen the likelihood of thermal damage to at least the outer layers of the epidermis. Depths of tissue that are not significantly cooled by pre-cooling will be heated to therapeutic temperatures resulting in the desired therapeutic effect. The amount or duration of pre-cooling may be used to select the protected depth of untreated tissue. Lengthier durations of pre-cooling produce a deeper protected zone in the tissue, while the converse situation occurs for shorter periods of pre-cooling.

After a short interval to permit the tissue to be cooled to a targeted pre-cool temperature, system controller 18 actuates switch 46 of multiplexer 44 to close the current path between electrode 24 and generator 42. The other switches 48, 50, 52 remain in an open condition so that the circuits to electrodes 26, 28, 30 are open and unpowered. Actuating switch 46 causes the electrode 24 to be energized by the high frequency generator 42 to deliver high frequency energy over a first time period to treat the first region of the tissue beneath the electrode 24 and around its edges 32, 36. The active electrode 24 transmits high frequency energy to the skin according to the power profile with the power levels 60-69 depicted in FIG. 4 while serving as a skin contact cooling membrane for the cryogen. If needed, additional amounts of coolant may be delivered to sustain a suitable cooling profile for removing heat from the patient's tissue during, before, or after energization of any or all of the active electrodes 24, 26, 28, 30.

The system controller 18 monitors a combination of inputs, such as temperatures, power levels and delivery duration, to precisely and safely control the high frequency energy and cooling delivery to each treatment site in the grid. During treatment using the energized active electrode 24, the handpiece 12 and system controller 18 cooperate to process information received from the treatment tip 14 about skin temperature, skin contact, treatment force, and/or pressure against the skin; cooling system function,; and other types of relevant data in order to generate the proper high frequency signal at the generator 42 and appropriate cooling.

At the conclusion of the first repetition with electrode 24, switch 46 of multiplexer 44 is opened by system controller 18 to open the current path from the generator 42 to electrode 24. The system controller 18 actuates switch 48 to a closed position to close the circuit with the generator 42 and a second tissue region proximate to electrode 26 is then treated with high frequency energy. Switches 46, 50 and 52 of the multiplexer 44 remain open so that active electrodes 24, 28, 30 are unpowered. The power is delivered to the active electrode 26 and to the treated tissue according to the power profile depicted in FIG. 4. Because the second tissue region has already been pre-cooled, high frequency energy may be delivered to the second tissue region over a second time period with a minimal time delay after the end of the first time period. While the second tissue region is being treated over the second time period, the first region receives a post-cooling treatment. A third tissue region proximate to electrode 28 is pre-cooled in anticipation of subsequent treatment with high frequency energy at the conclusion of the second time period. In a similar manner, the multiplexer 44 is used to serially close the current path between a respective one of the active electrodes 28, 30 of the treatment electrode 20 and the generator 42 to treat the third tissue region proximate to electrode 28 and a fourth tissue region proximate to electrode 30. The power is delivered to these active electrodes 28, 30 and to the treated tissue according to the power profile depicted in FIG. 4.

As a result of the switching on and off of the electrodes, the active electrodes 24, 26, 28, 30 are sequentially energized by generator 42 to deliver high frequency energy to different regions of the patient's tissue beneath the skin surface while the treatment electrode 20 is proximate but external to the skin surface. Only one of the active electrodes 24, 26, 28, 30 is energized with high frequency energy at any instant in time, although multiple electrodes or groups of electrodes may be energized at any one time.

The coolant may also be used to cool portions of the tissue regions after heating by the transferred high frequency energy from active electrodes 24, 26, 28, 30. Post-cooling may prevent or reduce heat delivered deeper into the tissue from conducting outward toward the skin surface and heating shallower tissue regions, such as the epidermis, to temperatures which could burn the epidermis even though the external energy delivery to the targeted tissue has ceased.

After energy delivery is completed from all of the active electrodes 24, 26, 28, 30 and any post-cooling is completed, the handpiece 12 is maneuvered to lift the portion of the treatment electrode 20 from the skin surface. The handpiece 12 and treatment tip 14 are moved among subsequent treatment locations in the grid and energy is delivered is a similar manner for treating large regions on the patient, such as the patient's face. Power is delivered to each of the active electrodes 24, 26, 28, 30 and to the treated tissue at each of the subsequent treatment locations according to the power levels 60-69 of the power profile depicted in FIG. 4. Multiple passes over the entire grid of the treatment zone, separated in time by a quiescent period of a few minutes, may be used to enhance the treatment, as understood by persons skilled in the art. Multiple treatments, which are separated temporally by a lengthier healing period, may be needed for a treatment that supplies the desired cosmetic effect.

Figure 5:
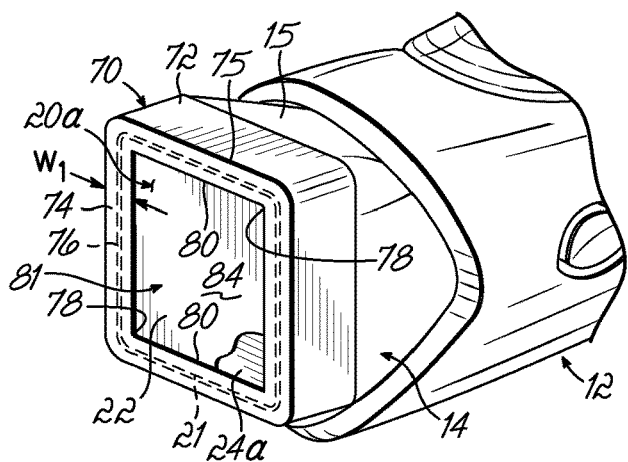
FIG. 5 is a partial perspective view of the handpiece and treatment tip of FIG. 1 in which an electrically-insulating sleeve in accordance with an embodiment of the invention is applied to the treatment tip.

With reference to FIG. 5 and in accordance with an embodiment of the invention, an electrically-insulating sleeve 70 is applied to the forward end of the treatment tip 14. In the representative embodiment, the treatment tip 14 is equipped with a single treatment electrode 20a having a single active electrode 24a composed of electrical conductor on substrate 22, rather than populated with the plurality of active electrodes 24, 26, 28, 30 (FIG. 3). The sleeve 70 includes a skirt 72 that wraps about the treatment tip 14 and a tip frame 74 that encircles the active electrode 24a of the treatment electrode 20a. The skirt 72 secures the sleeve 70 to the treatment tip 14 and intersects the tip frame 74 at a corner extending circumferentially about an outer edge 75 of the frame 74. The skirt 72 and tip frame 74 have a unitary structure or, alternatively, may have an integral construction in which multiple components are joined together.

The sleeve 70 is preferably composed of a solid electrically-insulating material or a dielectric material that is a poor conductor of electricity, but an efficient supporter of electrostatic fields established by the alternating high frequency electric field from the active electrode 24a. In one embodiment, the sleeve 70 may be composed of a sheet of a thin flexible base polymer film such as polyimide or another material characterized by a relatively high electrical resistivity and a relatively high thermal conductivity. In another embodiment, the sleeve 70 may be composed of a thin sheet of a material identical to the material from which the substrate 22 of the treatment electrode 20a is composed.

In various embodiments, the sleeve 70 may have a thickness within the range of 1 millimeter to 2 millimeters.

The tip frame 74 extends inwardly from the outer edge 75 with a width, $w_1$, that is sufficient to overlap a small gap 76 that exists between the outer side edge of the treatment electrode 20a and the inner side edge of the housing 15 of the treatment tip 14. The tip frame 74 includes a plurality of inside edges 80 that intersect at approximately right angles and a plurality of inside corners 78 defined by the inside edges 80. The inside edges 80 delineate an inner perimeter that extends about the entire circumference of the active electrode 24a of the treatment tip 14 and that defines an aperture or opening 81. In the representative embodiment, the width, $w_1$, of the tip frame 74 is uniform about the circumference. The opening 81, which is rectangular or square with right angle inside corners 78 in the representative embodiment, partially exposes the active electrode 24a. Varying the width, $w_1$, of the tip frame 74 changes the exposed area of the active electrode 24a. Preferably, the majority of the surface area of conductor composing the active electrode 24a is exposed by the opening 81. The outer peripheral edge 21 of the conductor constituting the active electrode 24a and gap 76 are overlapped and covered by the tip frame 74.

Figure 6:
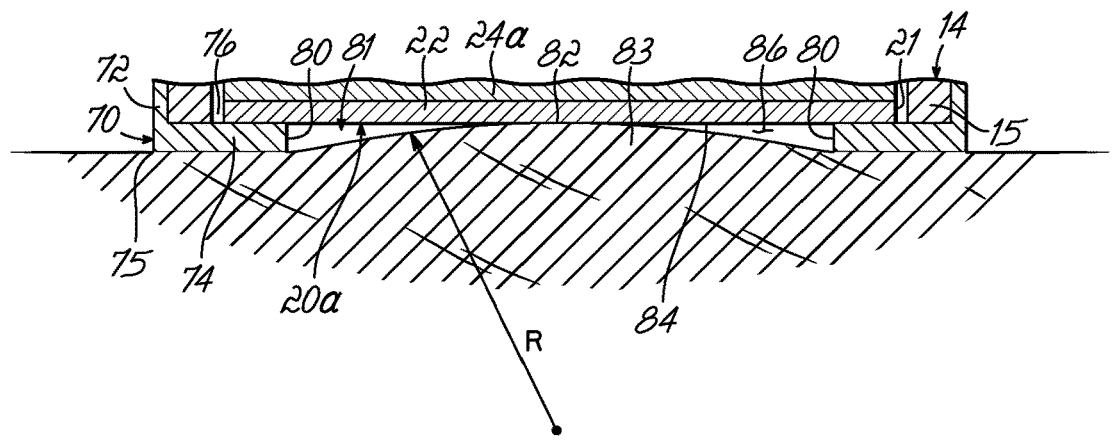
FIG. 6 is a cross-sectional view of the treatment tip and electrically-insulating sleeve of FIG. 5 during use.

The tip frame 74 of the sleeve 70 is interposed as a thin sheet of a dielectric material between the treatment tip 14 and the surface 82 of the skin 83 during a treatment repetition. As apparent in FIG. 6, the tip frame 74 is pressed against the skin surface 82 and operates as a spacer or standoff that separates a portion of the active electrode 24a of treatment electrode 20a from the skin surface to define a shallow cavity 86. Peripherally inside the inside edges 80 of the tip frame 74, the front surface 84 of the dielectric substrate 22 of the treatment electrode 20a has a contacting relationship with the skin surface 82. However, the portion of the skin surface 82 inside the inside edges 80 of the tip frame 74 is free to relax outwardly within the shallow cavity 86. As a result, the skin surface 82 contacting the front surface 84 of the treatment electrode 20a develops a curvature characterized by a relatively large radius of curvature, R. The resulting appearance of the skin surface 82 is more spherical than planar.

Figure 7:
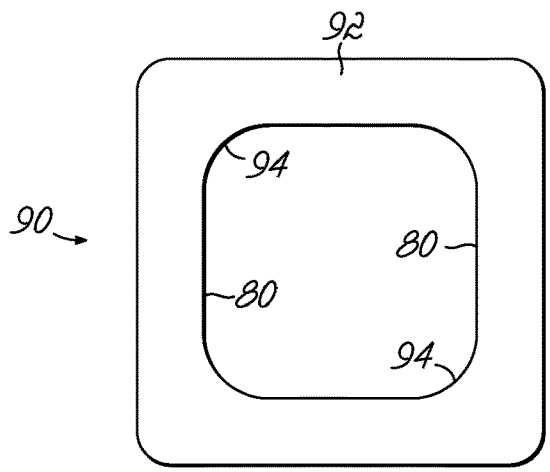
FIGS. 7-9 are front views of electrically-insulating sleeves in accordance with different alternative embodiments of the invention.

With reference to FIG. 7 and in accordance with an alternative embodiment of the invention, a sleeve 90 includes a tip frame 92 with a set of inside corners 94 that are modified to have a radius of curvature rather than right angle junctions, but is otherwise similar to sleeve 70 (FIGS. 5, 7).

Figure 8:
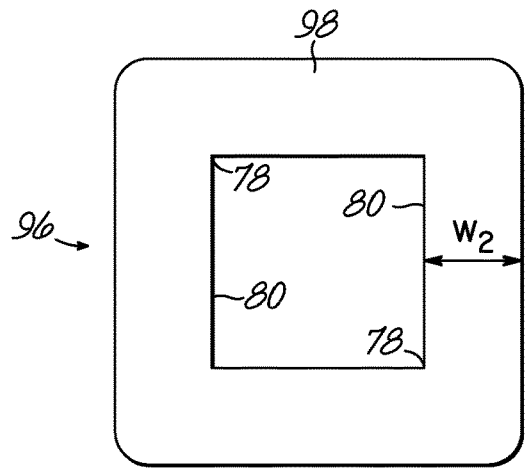

With reference to FIG. 8 and in accordance with another alternative embodiment of the invention, a sleeve 96 includes a frame 98 characterized by an increased width, $w_2$, in comparison with the tip frame 74 of sleeve 70 (FIGS. 5, 7), but is otherwise similar to sleeve 70.

Figure 9:
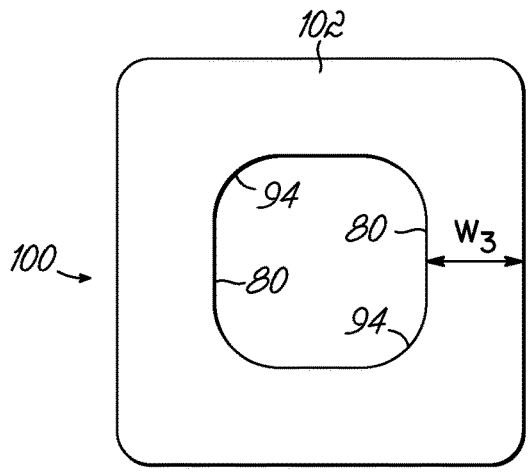

With reference to FIG. 9 and in accordance with yet another alternative embodiment of the invention, a sleeve 100 includes a frame 102 characterized by an increased width, $w_3$, in comparison with the width of frame 98 of sleeve 96 (FIG. 8), but is otherwise similar to sleeve 96 (FIG. 8).

The thickness of any of the frames 74, 92, 98, 102 may be selected to optimize the beneficial effects, as described below. Among other factors, increasing the thickness will operate to increase the radius of curvature, R, of the skin surface 82.

The sleeves 70, 90, 96, 100, which may be used in conjunction with treatment electrode 20a, treatment electrode 20 (FIGS. 1-3), or with any other similar type of treatment electrode, are believed to be effective in reducing the edge effect observed during treatment procedures. Specifically, the sleeves 70, 90, 96, 100 are believed to alleviate or mitigate overheating from the maximized energy density near the peripheral edge of the treatment electrode 20a. Consequently, the occurrence of hot spot thermal zones near the peripheral edges of the treatment electrode 20a is reduced. This permits higher treatment levels with an increased average energy density, in comparison with the absence of one of the sleeves 70, 90, 96, 100, for the high frequency energy delivered during the treatment procedure.

Figure 10:
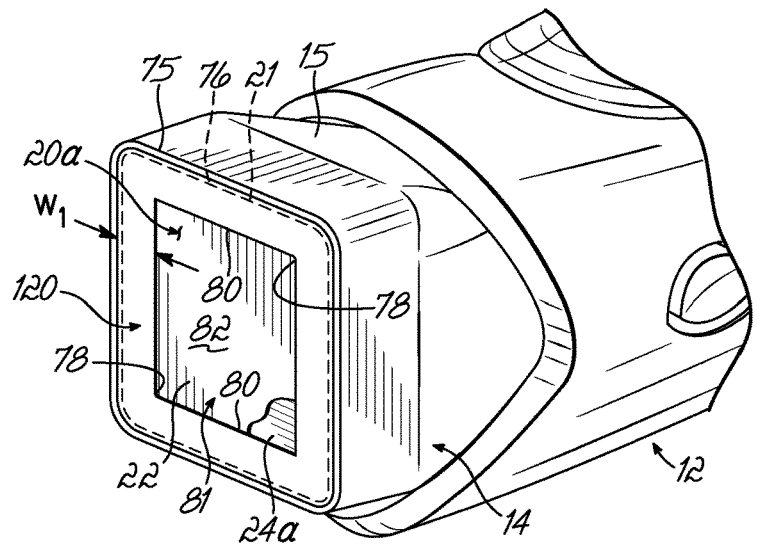
FIG. 10 is a partial perspective view of the handpiece and treatment tip to which is applied a tip frame composed of a dielectric material in accordance with an alternative embodiment of the invention.

With reference to FIG. 10 and in accordance with an embodiment of the invention, a tip frame 120 is directly applied or mounted to the exposed surface of the treatment electrode 20a at the forward end of the treatment tip 14. The tip frame 120 omits the skirt 72 found in sleeves 70, 90, 96, 100. However, similar to the tip frame 74 found in sleeves 70, 90, 96, 100, the tip frame 120 encircles the active electrode 24a and includes the aperture or opening 81 defined by inner edges 80. The tip frame 120 may be adhesively bonded to the substrate 22 of the treatment electrode 20a or may be integrally formed with the substrate 22 of treatment electrode 20a. The tip frame 120 may be composed of the same solid electrically-insulating material or dielectric material as the sleeves 70, 90, 96, 100.

The tip frame 120 extends inwardly from the outer edge 75 with a width, $w_1$, that is sufficient to overlap the gap 76 that exists between the outer side edge of the treatment electrode 20a and the inner side edge of the housing 15 of the treatment tip 14. The inside corners 78 of the tip frame 120 are defined by the inside edges 80 that intersect at approximately right angles. However, the inside edges 80 may be modified as shown in FIGS. 7 and 9 and the width of the tip frame 120 may be modified as shown in FIGS. 8 and 9. The inside edges 80 define an inner perimeter that extends about the entire circumference of the active electrode 24a of treatment electrode 20a. In the representative embodiment, the width, $w_1$, of the tip frame 120 is circumferentially uniform. The opening 81, which is rectangular or square with right angle inside corners 78 in the representative embodiment, partially exposes the active electrode 24a. Varying the width, $w_1$, of the tip frame 120 changes the exposed surface area of active electrode 24a. The tip frame 120 is interposed between the substrate 22 of treatment electrode 20a and the skin surface 82 during a treatment repetition such that the arrangement is similar to that shown in FIG. 6.

Figure 11A:
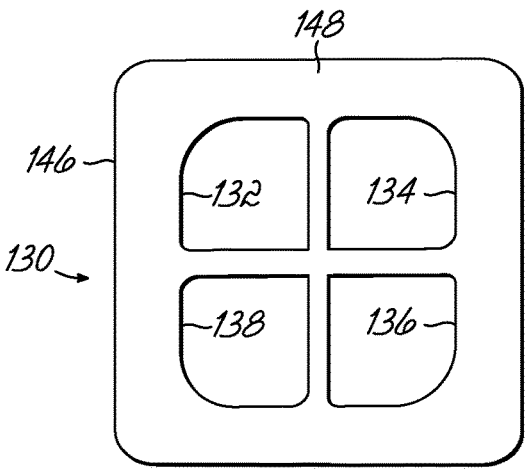
FIG. 11A is a front view of the tip frame of FIG. 11.
Figure 11:
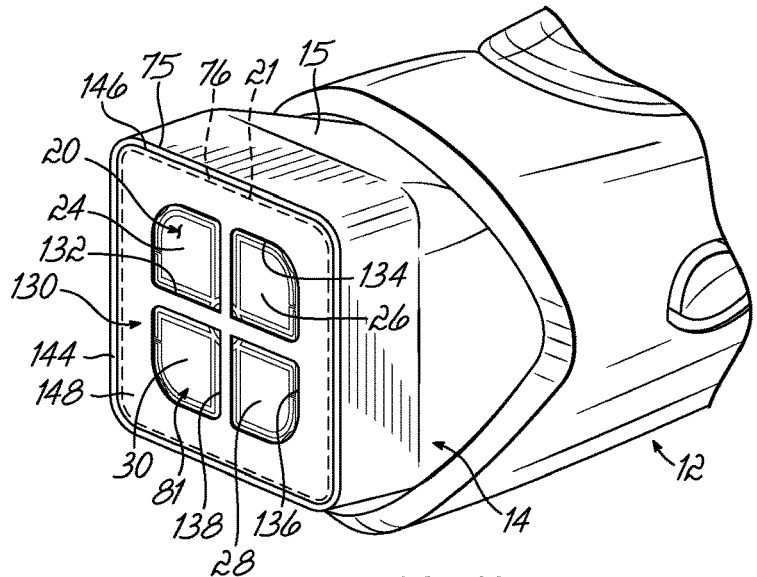
FIG. 11 is a partial perspective view of the handpiece and treatment tip to which is applied a tip frame composed of a dielectric material in accordance with an alternative embodiment of the invention.
Figure 12:
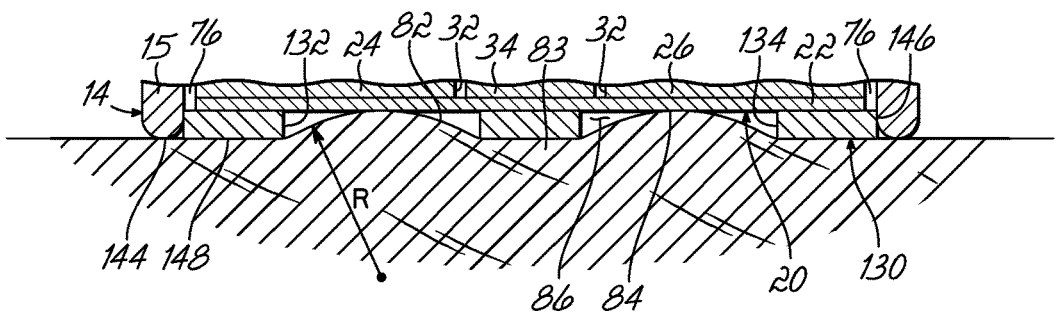
FIG. 12 is a cross-sectional view of the treatment tip and tip frame of FIG. 11 during use.

With reference to FIGS. 11, 11A, and 12 and in accordance with an embodiment of the invention, a tip frame 130 is directly applied or mounted to the exposed surface of the substrate 22 of treatment electrode 20. Similar to tip frame 120 (FIG. 10), tip frame 130 omits the skirt 72 found in sleeves 70, 90, 96, 100. The tip frame 130 includes a plurality of apertures or openings 132, 134, 136, 138 that coincide numerically with the number of active electrodes 24, 26, 28, 30. An inner perimeter of each of the openings 132, 134, 136, 138 includes a combination of linear and curved inner edges that are arranged to provide an aperture shape that matches the shape of the corresponding one of the active electrodes 24, 26, 28, 30. The tip frame 130 may be adhesively bonded to the substrate 22 of the treatment electrode 20 or may be integrally formed with the substrate 22 of the treatment electrode 20.

The tip frame 130 is preferably composed of a solid electrically-insulating material or a dielectric material that is a poor conductor of electricity, but an efficient supporter of electrostatic fields established by an alternating electric field emitted by the active electrodes 24, 26, 28, 30 of treatment electrode 20 during energy delivery. In one embodiment, the tip frame 130 may be composed of a thin sheet of a flexible base polymer film such as polyimide or another material characterized by a relatively high electrical resistivity and a relatively high thermal conductivity. In another embodiment, the tip frame 130 and the substrate 22 of the treatment electrode 20 may be composed of the same material.

As apparent in FIG. 12, the tip frame 130 is pressed against the skin surface 82 and operates as a spacer or standoff that separates the substrate 22 of the treatment electrode 20 from the skin surface. Peripherally inside the inside edges surrounding each of the openings 132, 134, 136, 138 in the tip frame 130, a front surface 140 of each of the substrate overlying each of the active electrodes 24, 26, 28, 30 has a contacting relationship with the skin surface 82. However, the portion of the skin surface 82 inside the inside edges surrounding the openings 132, 134, 136, 138 is free to relax outwardly such that the surface 82 of the skin 83 develops a curvature characterized by a radius of curvature, R.

The housing 15 of the treatment tip 14 includes a rim 144 that encircles the forward end of the treatment electrode 20. An outer peripheral edge 146 of the tip frame 130 is arranged laterally inside of the rim 144 with a circumscribed relationship relative to the rim 144. The tip frame 130 is slightly recessed axially relative to the rim 144 such that the housing 15 proximate to the rim 144 covers the outer peripheral edge 146. In one embodiment, the front surface 148 of the tip frame 130 is flush (or co-planar) with the rim 144. This spatial relationship ensures that the outer peripheral edge 146 of the tip frame 130 cannot contact the skin surface 82 when the tip frame 130 is pressed against the skin surface 82. For example, the process fabricating the tip frame 130 may provide an outer peripheral edge 146 that is sharp or rough, which may result in patient discomfort, and the outer peripheral edge 146 of the tip frame 130 shields the skin surface 82 from the sharp or rough outer peripheral edge 146.

References herein to terms such as "vertical", "horizontal", etc. are made by way of example, and not by way of limitation, to establish a frame of reference. It is understood that various other frames of reference may be employed for describing the invention without departing from the spirit and scope of the invention. It is also understood that features of the invention are not necessarily shown to scale in the drawings. Furthermore, to the extent that the terms "composed of", "includes", "having", "has", "with", or variants thereof are used in either the detailed description or the claims, such terms are intended to be inclusive and open-ended in a manner similar to the term "comprising".

It will be understood that when an element is described as being "attached", "connected", or "coupled" to another element, it can be directly connected or coupled to the other element or intervening elements may be present. In contrast, when an element is described as being "directly attached", "directly connected", or "directly coupled" to another element, there are no intervening elements present.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

While the invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. Thus, the invention in its broader aspects is therefore not limited to the specific details, representative apparatus and method, and illustrative example shown and described. Accordingly, departures may be made from such details without departing from the spirit or scope of applicants' general inventive concept.

What is claimed is:

1. An apparatus comprising:
    a treatment tip including a treatment electrode, the treatment electrode having a substrate and a first active electrode on the substrate, the substrate composed of a dielectric material, the first active electrode composed of an electrical conductor, the substrate including a surface, the first active electrode configured to deliver electromagnetic energy to tissue beneath a skin surface, and the substrate arranged between the first active electrode and the skin surface when delivering the electromagnetic energy to the tissue; and
    a tip frame attached to the treatment tip, the frame composed of an electrically-insulating material, the tip frame including a first opening having an inner edge and an outer peripheral edge, and the first opening arranged relative to the treatment electrode to expose a first portion of the first active electrode and to cover a second portion of the first active electrode,
    wherein the tip frame provides a standoff from the surface of the substrate defining a first cavity surrounded by the inner edge of the first opening, and the second portion of the first active electrode is located between the outer peripheral edge of the first opening in the tip frame and the inner edge of the first opening in the tip frame.

2. The apparatus of claim 1 wherein the treatment electrode includes a second active electrode on the substrate, the second active electrode is configured to deliver the electromagnetic energy to the tissue beneath the skin surface, and the substrate is arranged between the second active electrode and the skin surface when delivering the electromagnetic energy to the tissue.

3. The apparatus of claim 2 wherein the first active electrode and the second active electrode are configured to be individually energized to deliver the electromagnetic energy to the tissue.

4. The apparatus of claim 2 wherein the tip frame includes a second opening having an inner edge and an outer peripheral edge, and the second opening arranged relative to the treatment electrode to expose a first portion of the second active electrode and to cover a second portion of the second active electrode.

5. The apparatus of claim 4 wherein the tip frame defines a second cavity surrounded by the inner edge of the second opening, and the second portion of the second active electrode is located between the outer peripheral edge of the second opening in the tip frame and the inner edge of the second opening in the tip frame.

6. The apparatus of claim 1 further comprising:
    a temperature sensor configured to sense a temperature at the treatment electrode.

7. The apparatus of claim 6 wherein the temperature sensor is a thermistor or a thermocouple.

8. The apparatus of claim 1 further comprising:
    a pressure sensor.

9. The apparatus of claim 1 wherein the treatment electrode and the tip frame are flexible.

10. The apparatus of claim 1 wherein the tip frame is attached to the treatment electrode.

11. The apparatus of claim 1 wherein the dielectric material of the substrate and the electrically-insulating material of the tip frame have the same composition.

12. The apparatus of claim 1 wherein the tip frame is part of a sleeve, and the sleeve further includes a skirt configured to wrap about the treatment tip and to secure the sleeve to the treatment tip.

* * * * *